United States Patent
Scott et al.

(10) Patent No.: US 6,772,651 B2
(45) Date of Patent: Aug. 10, 2004

(54) SOIL SAMPLER LINER WITH AREAS OF REDUCED WALL THICKNESS

(75) Inventors: Gregory H. Scott, Salina, KS (US); Thomas M. Christy, Salina, KS (US); Michael E. Carlin, Salina, KS (US)

(73) Assignee: Kejr, Inc., Salina, KS (US)

( * ) Notice: Subject to any disclaimer, the term of this patent is extended or adjusted under 35 U.S.C. 154(b) by 36 days.

(21) Appl. No.: 09/888,907

(22) Filed: Jun. 25, 2001

(65) Prior Publication Data

US 2002/0194937 A1 Dec. 26, 2002

(51) Int. Cl.[7] .......................... E25B 25/06; E49B 49/02; E49B 49/00; G01N 1/08
(52) U.S. Cl. ...................... 73/864.91; 175/20; 283/202
(58) Field of Search .................... 73/864.91, 864.44, 73/864.51; 175/20, 58; 383/202; 53/475

(56) References Cited

U.S. PATENT DOCUMENTS

| | | | | |
|---|---|---|---|---|
| 2,287,059 A | * | 6/1942 | Platts et al. ............... | 175/20 X |
| 3,331,249 A | * | 7/1967 | Botrad ................ | 73/864.45 X |
| 3,872,935 A | * | 3/1975 | Miclke ..................... | 175/20 X |
| 4,611,350 A | * | 9/1986 | Kaczerwaski .................. | 383/7 |
| 5,038,624 A | * | 8/1991 | Clay ........................ | 73/864.44 |
| 5,417,122 A | * | 5/1995 | Casey et al. ............. | 73/864.44 |
| 5,450,913 A | * | 9/1995 | Mefferd et al. ................ | 175/58 |
| 5,488,876 A | * | 2/1996 | Casey et al. ............. | 73/864.44 |
| 5,542,481 A | * | 8/1996 | Scott ........................... | 175/23 |
| 5,606,139 A | * | 2/1997 | Wittig et al. ............. | 73/864.44 |
| 2003/0205408 A1 | * | 11/2003 | Lee et al. ..................... | 175/20 |
| 2004/0035607 A1 | * | 2/2004 | Jacobs et al. ................. | 175/20 |

* cited by examiner

*Primary Examiner*—Thomas P. Noland
(74) *Attorney, Agent, or Firm*—Shook, Hardy & Bacon LLP

(57) ABSTRACT

A soil sampler liner with areas of reduced wall thickness is defined by a continuous wall that has a reduced area extending along at least a portion of the length of the liner. The liner is inserted into the inner bore of a sampler probe, and a soil sample is taken by vertically inserting the probe and liner into the ground. The wall of the liner has at least two distinct areas of varying thickness; a reduced wall area and wall areas adjacent to the reduced wall area. The walls are sufficiently strong to withstand the forces applied to the liner when taking relatively large-diameter soil samples. The thickness of the wall at the reduced wall area is less than the thickness of the wall at the adjacent areas to permit a user to easily and safely cut through the wall at the reduced wall area and remove a large-diameter soil sample from the liner. The liner is also radially compressible into a flattened shape for compact and economical packaging and shipment of liners in relatively large quantities.

4 Claims, 1 Drawing Sheet

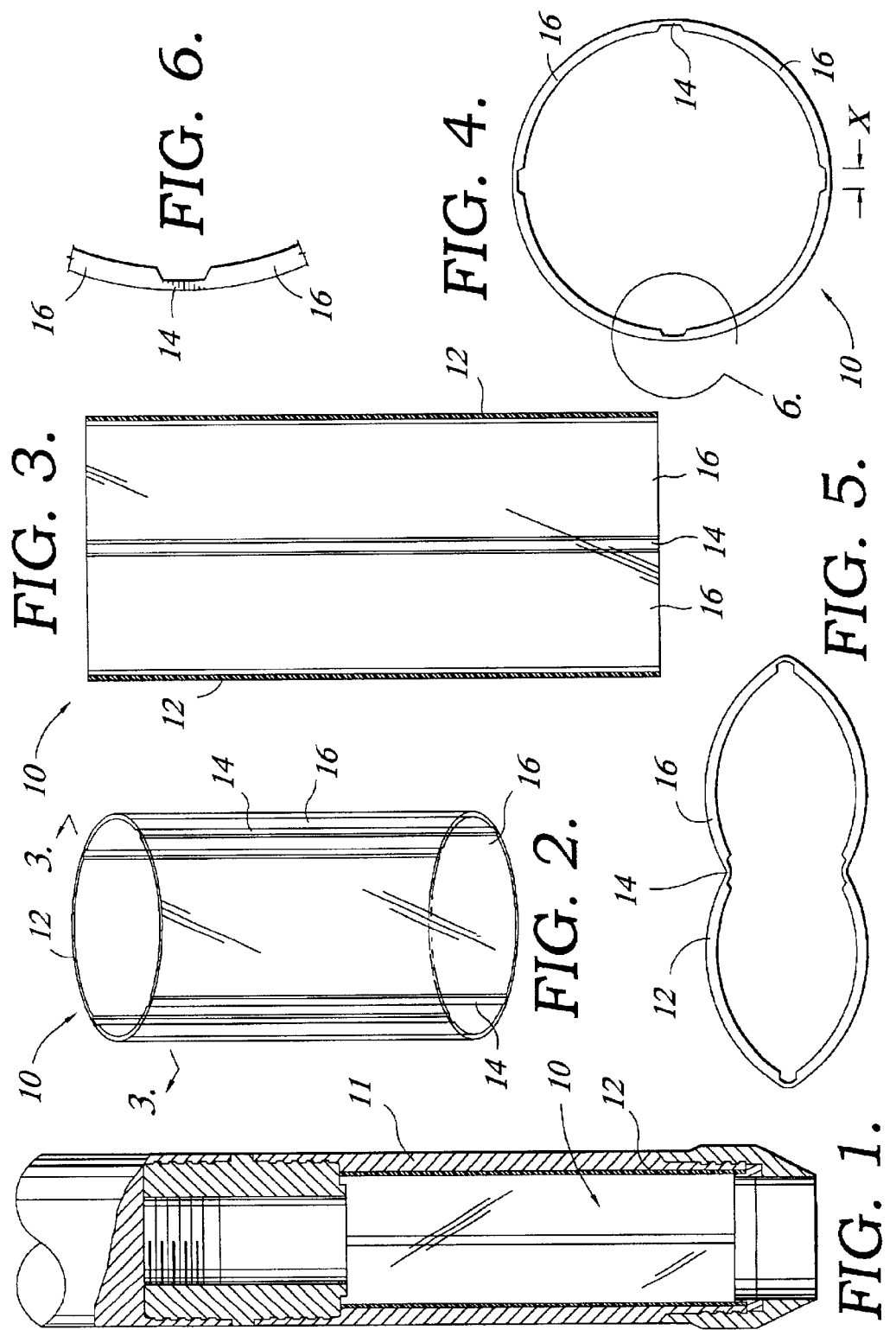

US 6,772,651 B2

SOIL SAMPLER LINER WITH AREAS OF REDUCED WALL THICKNESS

STATEMENT REGARDING FEDERALLY SPONSORED RESEARCH OR DEVELOPMENT

Not applicable.

CROSS-REFERENCE TO RELATED APPLICATIONS

Not applicable.

BACKGROUND OF THE INVENTION

This invention relates generally to soil sampling, and more particularly to liners for use in collecting a soil sample.

Soil samples are frequently taken from agricultural fields and other ground to obtain information about the soil, including its organic content, mineral content and pollutant levels. Soil samples are generally obtained by inserting a probe rod into the soil to capture a sample and then withdrawing the probe rod and sample from the soil. To facilitate handling of the soil sample, sampler liners are often used; these liners fit within the probe rod and encase the sample. The soil sample is removed from the liner by cutting (usually manually) along the length of the liner, spreading the liner to expose the soil sample, and lifting the sample from the liner.

Soil samples of relatively large cross-sectional area are often desirable. These larger samples call for liners with relatively thick walls that can withstand the axial and radial forces imposed upon the liner by the insertion process and the soil sample itself. Cutting these thicker-walled liners, however, has proven difficult (if not impossible) and dangerous. In addition, the liners are generally used only one time, and are then discarded; users may require several liners each day. Accordingly, the liners are typically shipped to the users in bulk, in quantities of approximately twenty five (25) per box. Because the liners are relatively rigid cylinders, however, a considerable amount of empty space (air) is shipped in each box; the liner material itself comprises a fairly small volume.

There is therefore a need for a soil sampler liner having sufficient strength to withstand the forces imposed upon it while allowing a user to remove a soil sample and permitting more compact and economical packaging and shipment of the liners.

SUMMARY OF THE INVENTION

Accordingly, it is an object of the present invention to provide a soil sampler liner allowing easy removal of the soil sample.

It is another object of the present invention to provide a soil sampler liner for taking large-diameter soil samples while allowing safe and efficient removal of the soil sample.

It is a further object of the present invention to provide a soil sampler liner capable of withstanding the axial and radial forces imposed upon the liner by larger-diameter soil samples while allowing a user to easily remove the soil sample from the probe and liner.

It is a further object of the invention to provide a soil sampler liner that can be easily and safely cut to enable a user to remove a soil sample from the liner.

It is yet another object of the present invention to provide a soil sampler liner that may be compactly and economically packaged and shipped in relatively large quantities.

Accordingly, the present invention provides for a soil sampler liner with areas of reduced wall thickness. The liner is defined by a continuous wall that has a reduced area extending along at least a portion of the length of the liner. The wall has at least two distinct areas of varying thickness; a reduced wall area and walls areas adjacent to the reduced wall area. The thickness of the wall at the reduced wall area is less than the thickness of the wall at the adjacent areas, to permit a user to easily and safely cut through the wall at the reduced wall area and expose the soil sample contained within the liner. The liner is radially compressible into a generally figure-eight shape for compact and economical packaging and shipment.

BRIEF DESCRIPTION OF THE DRAWINGS

In the accompanying drawings, which form a part of the specification and are to be read in conjunction therewith, and in which like reference numerals are used to indicate like parts in the various views:

FIG. 1 is a side elevational view showing the soil sampler liner inserted into the inner bore of a sampler probe rod, with parts broken away and shown in cross-section to reveal details of construction;

FIG. 2 is a perspective view showing the soil sampler liner according to the present invention;

FIG. 3 is a cross-sectional elevation view taken generally along line 3—3 of FIG. 2;

FIG. 4 is a top plan view of the soil sampler liner of FIG. 2;

FIG. 5 is a top plan view of the soil sampler liner of FIG. 2 radially compressed into a generally figure-eight shape for packaging and shipping; and FIG. 6 is an enlarged fragmentary view of the area indicated by the numeral 6 in FIG. 4 showing a reduced wall area (shaded) and adjacent wall areas.

DETAILED DESCRIPTION OF THE PREFERRED EMBODIMENTS

Referring to the drawings in greater detail, and initially to FIG. 1 a soil sampler liner of the present invention is designated generally by the numeral 10. In FIG. 1, liner 10 is shown inserted into the inner bore of a sampler probe 11. To obtain a soil sample, probe 11 and liner 10 are inserted vertically into the ground by hydraulic pressure, manual force, or other means to capture a soil sample within liner 10. Probe 11 and liner 10 are then withdrawn from the ground, liner 10 is removed from probe 11, and the soil sample is removed from liner 10 for analysis.

The embodiment of liner 10 depicted in FIG. 2 shows liner 10 defined by a continuous cylindrical wall 12. Liner 10 and wall 12 are depicted as being constructed of a substantially transparent plastic material. It will be understood, however, that liner 10 and wall 12 may be constructed of reinforced cardboard, fiberglass, opaque plastic, or any other material of sufficient strength to withstand both the axial forces applied to wall 12 when liner 10 is inserted into the soil during sampling and the radial forces applied to wall 12 from the soil sample contained within liner 10. However, the material must also be relatively easy to cut to enable the user to expose and remove the soil sample from liner 10, as described below.

As best seen in FIGS. 4 and 6, wall 12 has at least two distinct areas of varying thickness; the reduced wall area 14 extending along at least a portion of the length of the liner 10, and the wall areas 16 adjacent to reduced wall area 14.

The thickness of wall 12 at reduced wall area 14 is less than the thickness of wall 12 at adjacent wall areas 16. FIG. 6 depicts reduced wall area 14 shaded to distinguish reduced wall area 14 from unshaded adjacent wall areas 16. As best seen in FIG. 6, the reduced wall areas 14 are preferably defined by forming one or more "steps" or indentations in the inner diameter of wall 12, while the outer diameter of wall 12 remains constant at all points along the periphery of wall 12.

In one embodiment, the thickness of wall 12 at reduced wall area 14 is approximately 0.02 inches and the thickness of wall 12 at adjacent wall areas 16 is approximately 0.05 inches. It will be understood that these dimensions may vary, but that wall 12 must be sufficiently thick to withstand the forces applied to liner 10 and sufficiently thin at reduced wall area 14 to allow wall 12 to be relatively easily cut at reduced wall area 14. The circumferential width "X" (see FIG. 4) of the reduced wall area 14 varies depending on the length of liner 10, the thickness of wall 12, and the particular soil application, but is generally approximately 0.2". Width "X" of reduced wall area 14 must be sufficient to receive a blade.

In one embodiment, the inner diameter of liner 10, measured at adjacent wall areas 14, is approximately 2.5 inches. It will be understood that the inner diameter of liner 10 will depend on the desired size of soil sample, the type of soil data to be obtained, the soil conditions, and other variables. The length of liner 10 generally varies from three feet to five feet, but can be any other suitable length. Reduced wall area 14 extends along at least a portion of the length of the liner 10, and may extend along the entire length of liner 10.

As best seen in FIG. 5, reduced wall areas 14 permit the liner 10 to be radially compressed such that wall 12 defines a compact, generally figure-eight shape. This enables liners 10 to be flattened during packaging and to be shipped in large quantities more efficiently and economically. It may be necessary to secure a wire, string, twist tie, or other retaining means around the compressed liner to retain the liner in its compressed figure-eight shape during packaging and shipment. The liners are restored to their original, uncompressed shape prior to use.

In operation, the user selects the desired length of the soil sample to be taken and uses a soil sampler liner 10 and soil sampler probe 11 having the appropriate corresponding length (e.g. 4 ft., 5 ft., or 1 meter). Soil sampler liner 10 is inserted into the inner bore of the probe 11, as shown in FIG. 1. Probe 11 and liner 10 are advanced vertically into the soil to the desired depth, thereby capturing a soil sample within liner 10. Probe 11, liner 10, and the soil sample are then raised and withdrawn from the soil. Liner 10, and the soil sample contained within liner 10, are removed from probe 11. The user then cuts through wall 12 of liner 10 at reduced wall area 14. Wall 12 of liner 10 is then spread apart at the incision to expose the soil sample, and the soil sample is removed from liner 10 for analysis.

It will be seen from the foregoing that the soil sampler liner with areas of reduced wall thickness allows for safe and easy removal of a soil sample from the liner, is sufficiently strong to withstand the axial and radial forces imposed upon the liner by taking large-diameter soil samples, and may be flattened for packaging to allow for compact and economical shipping in relatively large quantities.

It will also be seen from the foregoing that this invention is one well adapted to attain the ends and objects set forth above, and to attain other advantages which are obvious and inherent in the device. It will be understood that certain features and subcombinations are of utility and may be employed without reference to other features and subcombinations. This is contemplated by and within the scope of the claims. It will be appreciated by persons skilled in the art that the present invention is not limited to what has been particularly shown and described hereinabove. Rather, all matter shown in the accompanying drawings or described hereinabove is to be interpreted as illustrative and not limiting.

We claim:

1. A soil sampler liner comprising:

a liner member, said liner member defined by a continuous wall and having two reduced areas extending along at least a portion of the length of said member, said wall at said one or more reduced areas having a first thickness, said wall adjacent said one or more reduced areas having a second thickness, said second thickness being greater than said first thickness.

2. A soil sampler liner comprising:

a liner member, said liner member defined by a continuous wall and having four reduced areas extending along at least a portion of the length of said member, said wall at said one or more reduced areas having a first thickness, said wall adjacent said one or more reduced areas having a second thickness, said second thickness being greater than said first thickness.

3. A soil sampler liner comprising:

a tubular liner member, said liner member defined by a continuous wall and having one or more reduced areas extending along at least a portion of the length of said member, said wall at said one or more reduced areas having a first thickness, said wall adjacent said one or more reduced areas having a second thickness, said second thickness being greater than said first thickness, said wall adjacent said one or more reduced areas defining a generally figure-eight shape when said member is radially compressed.

4. A soil sampler liner comprising:

a tubular liner member, said liner member defined by a continuous wall and having one or more reduced areas extending along at least a portion of the length of said member, said wall at said one or more reduced areas having a first thickness, said wall adjacent said one or more reduced areas having a second thickness, said second thickness being greater than said first thickness, wherein the outer diameter of said liner member is constant at all points along the periphery of said liner member.

* * * * *